US012236592B2

(12) United States Patent
Islam et al.

(10) Patent No.: US 12,236,592 B2
(45) Date of Patent: Feb. 25, 2025

(54) SYSTEMS, METHODS, AND APPARATUSES FOR SYSTEMATICALLY DETERMINING AN OPTIMAL APPROACH FOR THE COMPUTER-AIDED DIAGNOSIS OF A PULMONARY EMBOLISM

(71) Applicant: Arizona Board of Regents on behalf of Arizona State University, Scottsdale, AZ (US)

(72) Inventors: Nahid Ul Islam, Mesa, AZ (US); Shiv Gehlot, Darwara (IN); Zongwei Zhou, Tempe, AZ (US); Jianming Liang, Scottsdale, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 325 days.

(21) Appl. No.: 17/944,881

(22) Filed: Sep. 14, 2022

(65) Prior Publication Data
US 2023/0081305 A1  Mar. 16, 2023

Related U.S. Application Data

(60) Provisional application No. 63/244,183, filed on Sep. 14, 2021.

(51) Int. Cl.
*G06T 7/00* (2017.01)
*A61B 6/50* (2024.01)
(Continued)

(52) U.S. Cl.
CPC .............. *G06T 7/0012* (2013.01); *A61B 6/50* (2013.01); *G06T 3/40* (2013.01); *G06V 10/7715* (2022.01);
(Continued)

(58) Field of Classification Search
None
See application file for complete search history.

(56) References Cited

U.S. PATENT DOCUMENTS 11,547,486 B1 *  1/2023  Roh ..................... G16H 50/50
11,672,614 B1 *  6/2023  Roh ..................... A61B 5/4504
                                              382/153

(Continued)

OTHER PUBLICATIONS

Zbontar, J. et al., "Barlow Twins: Self-Supervised Learning via Redundancy Reduction," International Conference on Machine Learning (PMLR), 2021, pp. 12310-12320.

(Continued)

*Primary Examiner* — Darryl V Dottin
(74) *Attorney, Agent, or Firm* — Elliott, Ostrander & Preston, P.C.

(57) ABSTRACT

Described herein are means for systematically determining an optimal approach for the computer-aided diagnosis of a pulmonary embolism, in the context of processing medical imaging. According to a particular embodiment, there is a system specially configured for diagnosing a Pulmonary Embolism (PE) within new medical images which form no part of the dataset upon which the AI model was trained. Such a system executes operations for receiving a plurality of medical images and processing the plurality of medical images by executing an image-level classification algorithm to determine the presence or absence of a Pulmonary Embolism (PE) within each image via operations including: pre-training an AI model through supervised learning to identify ground truth; fine-tuning the pre-trained AI model specifically for PE diagnosis to generate a pre-trained PE diagnosis and detection AI model; wherein the pre-trained AI model is based on a modified CNN architecture having introduced therein a squeeze and excitation (SE) block enabling the CNN architecture to extract informative fea- (Continued)

105 (a)    110 (b)    115 (c)    120 (d)    125 (e)    130 (f)

tures from the plurality of medical images by fusing spatial and channel-wise information; applying the pre-trained PE diagnosis and detection AI model to new medical images to render a prediction as to the presence or absence of the Pulmonary Embolism within the new medical images; and outputting the prediction as a PE diagnosis for a medical patient.

20 Claims, 14 Drawing Sheets

(51) Int. Cl.
    *G06T 3/40*     (2024.01)
    *G06V 10/77*     (2022.01)
    *G06V 10/774*     (2022.01)
    *G06V 10/82*     (2022.01)
    *G16H 50/20*     (2018.01)

(52) U.S. Cl.
    CPC ............ *G06V 10/774* (2022.01); *G06V 10/82* (2022.01); *G16H 50/20* (2018.01); *G06T 2207/20081* (2013.01); *G06T 2207/20084* (2013.01); *G06T 2207/30061* (2013.01); *G06T 2207/30101* (2013.01); *G06V 2201/03* (2022.01)

(56) References Cited

U.S. PATENT DOCUMENTS

2022/0198662 A1* 6/2022 Ay ....................... A61B 5/7267
2022/0208355 A1* 6/2022 Li ........................... G06T 7/174

OTHER PUBLICATIONS

Zhou, C., et al., "Computer-aided detection of pulmonary embolism in computed tomographic pulmonary angiography (CTPA): Performance evaluation with independent data sets," Medical Physics, vol. 36, Issue 8, 2009, pp. 3385-3396.
Zhou, Z. et al., "Active, continual fine tuning of convolutional neural networks for reducing annotation efforts," Medical Image Analysis, vol. 71, 2021, 101997, 15 pages.
Zhou, Z. et al., "Fine-tuning Convolutional Neural Networks for Biomedical Image Analysis: Actively and Incrementally," In 30th IEEE Conference on Computer Vision and Pattern Recognition, CVPR 2017, pp. 4761-4772, 2017.
Zhou, Z. et al., "Models Genesis: Generic Autodidactic Models for 3D Medical Image Analysis," Medical Image Computing and Computer Assisted Intervention-MICCAI 2019: 22nd International Conference, Shenzhen, China, Oct. 13-17, 2019, Proceedings, Part IV 22, 2019, Springer International Publishing, pp. 384-393.
Zhou, Z., "Towards Annotation-Efficient Deep Learning for Computer-Aided Diagnosis," PhD thesis, Arizona State University, 2021, 214 pages.
Asano, Y.M. et al., "Self-labelling via simultaneous clustering and representation learning," arXiv preprint arXiv:1911.05371v1 [cs.CV], 2019, 21 pages.
Asano, Y.M. et al., "Self-Labelling via Simultaneous Clustering and Representation Learning," arXiv preprint arXiv:1911.05371v3 [cs.CV], 2020, 22 pages.
Brown, T.B., et al., "Language Models are Few-Shot Learnings," Advances in Neural Information Processing Systems, 2020, pp. 1877-1901.
Brown, T.B., et al., "Language Models are Few-shot Learners," arXiv preprint arXiv:2005.14165v4 [cs.CL], 2020, 75 pages.
Carbonneau, M.,A., et al. "Multiple Instance Learning: A Survey of Problem Characteristics and Applications," arXiv preprint arXiv:1612.03365 (2016), 37 pages.
Caron, M. et al., "Deep Clustering for Unsupervised Learning of Visual Features," In Proceedings of the European Conference on Computer Vision (ECCV), 2018, pp. 132-149.
Caron, M. et al., "Unsupervised learning of visual features by contrasting cluster assignments," arXiv preprint arXiv:2006.09882v5 [cs.CV], 2021, 23 pages.
Chen, T. et al., "A simple framework for contrastive learning of visual representations," International Conference on Machine Learning, PMLR) 2020, pp. 1597-1607.
Chen, T. et al., "Big Self-Supervised Models are Strong Semi-supervised Learners," Advances in Neural Information Processing Systems (NeurIPS), vol. 33, 2020, pp. 22243-22255.
Chen, X. et al., "Improved Baselines with Momentum Contrastive Learning," arXiv preprint arXiv:2003.04297v1 [cs.CV], 2020, 3 pages.
Chollet, F., "Xception: Deep Learning with Depthwise Separable Convolutions," Proceedings of the IEEE Conference on Computer Vision and Pattern Recognition, 2017, pp. 1251-1258.
Colak, E. et al., "The RSNA Pulmonary Embolism CT Dataset," Radiology: Artificial Intelligence, vol. 3, No. 2, 2021, 7 pages.
Deng, S. et al., "Deep learning in digital pathology image analysis: a survey," Frontiers of Medicine, vol. 14, No. 1, 2020, pp. 470-487.
Devlin, J. et al., "BERT: Pre-training of Deep Bidirectional Transformers for Language Understanding," arXiv preprint arXiv: 1810.04805v1 [cs.CL], 2018, 16 pages.
Dosovitskiy, A. et al., "An Image is Worth 16x16 Words: Transformers for Image Recognition at Scale," arXiv preprint arXiv:2010.11929v2 [cs.CV] Jun. 3, 2021, 22 pages.
Gildenblat, J., et al., "Pytorch Library for Cam Methods," 2021, https://github.com/jacobgil/pytorch-grad-cam, 11 pages.
Grill, J.B. et al., "Bootstrap Your Own Latent: A New Approach to Self-supervised Learning," Advances in Neural Information Processing Systems, vol. 33, 2020, pp. 21271-21284.
Gutmann, M. et al., "Noise-contrastive estimation: A new estimation principle for unnormalized statistical models," Proceedings of the Thirteenth International Conference on Artificial Intelligence and Statistics, JMLR Workshop and Conference Proceedings, vol. 9, 2010, pp. 297-304.
Haghighi, F. et al., "Learning Semantics-enriched Representation via Self-discovery, Self-classification, and Self-restoration," Medical Image Computing and Computer Assisted Intervention-MICCAI 2020, Lecture Notes in Computer Science, vol. 12261, Springer International Publishing Cham (2020), pp. 137-147.
Haghighi, F. et al., "Transferable Visual Words: Exploiting the Semantics of Anatomical Patterns for Self-supervised Learning," IEEE Transactions on Medical Imaging, vol. 40, No. 10, 2021, pp. 2857-2868.
Han, K., et al., "Transformer in Transformer," Advances in Neural Information Processing Systems, vol. 34, 2021, p. 15908-15919.
He, K. et al., "Deep Residual Learning for Image Recognition", Proceedings of the IEEE Conference on Computer Vision and Pattern Recognition (CVPR), Jun. 2016, pp. 770-778.
He, K. et al., "Momentum Contrast for Unsupervised Visual Representation Learning," Proceedings of the IEEE/CVF Conference on Computer Vision and Pattern Recognition, 2020, pp. 9729-9738.
Hu, D. et al., "How Well Does Self-Supervised Pre-training Perform with Streaming Data?," arXiv preprint arXiv:2104.12081v3 [cs.LG], 2021, 23 pages.
Hu, J. et al., "Squeeze-and-Excitation Networks," Proceedings of the IEEE Conference on Computer Vision and Pattern Recognition, 2018, pp. 7132-7141.
Huang, G. et al., "Densely Connected Convolutional Networks," Proceedings of the IEEE Conference on Computer Vision and Pattern Recognition, 2017, pp. 2261-2269.
Huang, S.C. et al., "PENet—a scalable deep-learning model for automated diagnosis of pulmonary embolism using volumetric CT imaging." NPJ Digital Medicine vol. 3, No. 1, Article No. 61, 2020, 9 pages.
Ilse, M., et al., "Attention-based Deep Multiple Instance Learning," International Conference on Machine Learning, Proceedings of Machine Learning Research, PLMR, 2018, pp. 2127-2136.
Islam, N.U., et al., "Seeking an Optimal Approach for Computer-Aided Pulmonary Embolism Detection," 16 pages.

(56) References Cited

OTHER PUBLICATIONS

Jing, L., et al., "Self-Supervised Visual Feature Learning with Deep Neural Networks: A Survey," IEEE Transactions on Pattern Analysis and Machine Intelligence, vol. 43, No. 11, 2021, pp. 4037-4058.

Leavitt, M.O., "Surgeon General's call to action to prevent deep vein thrombosis and pulmonary embolism," 2009, DIANE Publishing.

Liang, J. et al., "Computer Aided Detection of Pulmonary Embolism with Tobogganing and Multiple Instance Classification in CT Pulmonary Angiography", Biennial International Conference Information Processing in Medical Imaging, Springer, 2007, pp. 630-641.

Litjens, G. et al., "A Survey on Deep Learning in Medical Image Analysis," Medical Image Analysis, vol. 42, 2017, pp. 60-88.

Lucassen, W.A. et al. "Concerns in using multi-detector computed tomography for diagnosing pulmonary embolism in daily practice. A cross-sectional analysis using expert opinion as reference standard," Thrombosis Research, vol. 131, No. 2, 2013, pp. 145-149.

Masutani, Y. et al., "Computerized Detection of Pulmonary Embolism in Spiral CT Angiography Based on Volumetric Image Analysis," IEEE Transactions on Medical Imaging, vol. 21, No. 12, 2002, pp. 1517-1523.

Misra, I. et al. "Self-Supervised Learning of Pretext-Invariant Representations," Proceedings of the IEEE/CVF Conference on Computer Vision and Pattern Recognition, 2020, pp. 6707-6717.

Rajan, D. et al., "Pi-PE: A Pipeline for Pulmonary Embolism Detection using Sparsely Annotated 3D CT Images," Proceedings of Machine Learning Research Machine Learning for Health, ML4H, 2020, pp. 220-232.

Shin, H.C. et al., "Deep Convolutional Neural Networks for Computer-Aided Detection: CNN Architectures, Dataset Characteristics and Transfer Learning," IEEE Transactions on Medical Imaging, vol. 35, No. 5, 2016, pp. 1285-1298.

Stein, A., et al., "RSNA STR Pulmonary Embolism Detection," https://www.kaggle.com/c/rsna-str-pulmonary-embolism-detection/overview, 2020. Online; accessed Jun. 21, 2021.

Stein, A., et al., "RSNA STR Pulmonary Embolism Detection," Kaggle https://www.kaggle.com/c/rsha-str-pulmonary-embolism-detection/discussion/194145 (2020), 11 pages.

Stein, P.D. et al., "Multidetector Computed Tomography for Acute Pulmonary Embolism," The New England Journal of Medicine, vol. 354, No. 22, 2006, pp. 2317-2327.

Tajbakhsh, N. et al., "Computer-Aided Pulmonary Embolism Detection Using a Novel Vessel-aligned Multi-planar Image Representation and Convolutional Neural Networks," Medical Image Computing and Computer-Assisted Intervention—MICCAI 2015: 18th International Conference, Munich, Germany, Oct. 5-9, 2015, Proceedings, Part II 18, 2015, Springer International Publishing, pp. 62-69.

Tajbakhsh, N. et al., "Convolutional Neural Networks for Medical Image Analysis: Full Training or Fine Tuning?," IEEE Transactions on Medical Imaging, vol. 35, No. 5, May 2016, pp. 1299-1312.

Tian, Y. et al., "What Makes for Good Views for Contrastive Learning?," Advances in Neural Information Processing Systems, vol. 33, 2020, pp. 6827-6839.

Touvron, H. et al., "Training data-efficient image transformers & distillation through attention," Proceedings of the 38th International Conference on Machine Learning. PMLR, vol. 139, 2021, pp. 10347-10357.

U.S. Department of Health and Human Services Food and Drug Administration, "The Surgeon General's Call to Action to Prevent Deep Vein Thrombosis and Pulmonary Embolism," vol. 119, Issue 15, 2009, pp. e480-e482.

Vaswani, A. et al., "Attention Is All You Need," Advances in Neural Information Processing Systems, 2017, pp. 5998-6008.

Wu, Z. et al., "Unsupervised Feature Learning via Non-Parametric Instance Discrimination," Proceedings of the IEEE Conference on Computer Vision and Pattern Recognition (CVPR), 2018, pp. 3733-3742.

Xie, S. et al., "Aggregated Residual Transformations for Deep Neural Networks," Proceedings of the IEEE Conference on Computer Vision and Pattern Recognition (CVPR), 2017, pp. 1492-1500.

Yu, F. et al., "Dilated Residual Networks," Proceedings of the IEEE Conference on Computer Vision and Pattern Recognition (CVPR), 2017, pp. 472-480.

\* cited by examiner

FIG. 2A ← 201

TABLE 1:

| PE AUC with vision transformer (ViT) | | | | |
|---|---|---|---|---|
| Model | Image Size | Patch Size | Initialization | Val AUC |
| SeXception | 576 | NA | ImageNet | 0.9634 |
| ViT-B_32 | 512 | 32 | Random | 0.8212 |
| ViT-B_32 | 224 | 32 | ImageNet21k | 0.8456 |
| ViT-B_32 | 512 | 32 | ImageNet21k | 0.8847 |
| ViT-B_16 | 512 | 16 | Random | 0.8385 |
| ViT-B_16 | 224 | 16 | ImageNet21k | 0.8820 |
| ViT-B_16 | 512 | 16 | ImageNet21k | 0.9065 |
| ViT-B_16 | 576 | 16 | ImageNet21k | *0.9179* |

TABLE 2:

| Labels | SeResNext50 | Xception | SeXception | DenseNet121 | ResNet18 | ResNet50 |
|---|---|---|---|---|---|---|
| NegExam PE | 0.9137 | 0.9242 | 0.9261 | 0.9168 | 0.9141 | 0.9061 |
| Indeterminate | 0.8802 | 0.9168 | 0.8857 | 0.9233 | 0.9014 | 0.9278 |
| Left PE | 0.9030 | 0.9119 | 0.9100 | 0.9120 | 0.9000 | 0.8965 |
| Right PE | 0.9368 | 0.9410 | 0.9455 | 0.9380 | 0.9303 | 0.9254 |
| Central PE | 0.9543 | 0.9500 | 0.9487 | 0.9549 | 0.9445 | 0.9274 |
| RV LV Ratio≥1 | 0.8922 | 0.8924 | 0.8901 | 0.8804 | 0.8682 | 0.8471 |
| RV LV Ratio<1 | 0.8630 | 0.8722 | 0.8771 | 0.8708 | 0.8688 | 0.8719 |
| Chronic PE | 0.7254 | 0.7763 | 0.7361 | 0.7460 | 0.6995 | 0.6810 |
| Acute&Chronic PE | 0.8598 | 0.8352 | 0.8473 | 0.8492 | 0.8287 | 0.8398 |
| Mean AUC | 0.8807 | 0.8912 | 0.8852 | 0.8879 | 0.8728 | 0.8692 |

TABLE 3:

| Backbone | Parameters | Random | ImageNet |
|---|---|---|---|
| ResNet50 | 23,510,081 | 0.9037±0.0132 | 0.9473±0.0012 |
| DRN-A-50 | 23,510,081 | 0.9122±0.0096 | 0.9496±0.0011 |
| ResNet18 | 11,177,025 | 0.8874±0.0166 | 0.9520±0.0007 |
| DenseNet121 | 6,954,881 | 0.9317±0.0060 | 0.9543±0.0011 |
| SeResNet50 | 28,090,073 | 0.8654±0.0293 | 0.9573±0.0013 |
| SeNet154 | 27,561,945 | 0.8784±0.0292 | 0.9607±0.0012 |
| Xception | 20,809,001 | 0.9484±0.0013 | 0.9607±0.0007 |
| SeResNext50 | 27,561,945 | 0.8746±0.0486 | 0.9614±0.0011 |
| SeXception | 21,548,446 | 0.9498±0.0025 | 0.9634±0.0009 |

Tabular Results of Graphs at Figures 3A and 3B

TABLE 4:

| Pre-training | Mean AUC |
|---|---|
| Random | 0.9037±0.0132 |
| ImageNet | 0.9473±0.0012 |
| pirl | 0.8917±0.0261 |
| moco-v2 | 0.8920±0.0292 |
| moco-v1 | 0.9029±0.0192 |
| infomin | 0.9036±0.0184 |
| insdis | 0.9116±0.0111 |
| simclr-v2 | 0.9366±0.0029 |
| pcl-v2 | 0.9378±0.0031 |
| pcl-v1 | 0.9434±0.0020 |
| simclr-v1 | 0.9545±0.0011 |
| byol | 0.9563±0.0005 |
| swav | 0.9563±0.0010 |
| barlow-twins | 0.9566±0.0007 |
| sela-v2 | 0.9568±0.0029 |
| deepcluster-v2 | 0.9568±0.0006 |

Tabular Results of Graph at Figure 5A

FIG. 6

TABLE 5:

| Architecture | SeResNeXT50 | | | Xception | | | SeXception | | |
|---|---|---|---|---|---|---|---|---|---|
| Labels/Pooling | AMP | MP | AP | AMP | MP | AP | AMP | MP | AP |
| NegExam PE | 0.9138 | 0.9137 | 0.9188 | 0.9202 | 0.9202 | 0.9172 | 0.9183 | 0.9137 | 0.9201 |
| Indeterminate | 0.9144 | 0.9064 | 0.8986 | 0.8793 | 0.8580 | 0.8033 | 0.8616 | 0.8564 | 0.8499 |
| Left PE | 0.9122 | 0.9059 | 0.9086 | 0.9106 | 0.9100 | 0.9032 | 0.9042 | 0.9004 | 0.9024 |
| Right PE | 0.9340 | 0.9345 | 0.9373 | 0.9397 | 0.9366 | 0.9397 | 0.9403 | 0.9383 | 0.9412 |
| Central PE | 0.9561 | 0.9537 | 0.9520 | 0.9487 | 0.9465 | 0.9507 | 0.9472 | 0.9424 | 0.9453 |
| RV_LV Ratio≥1 | 0.8813 | 0.8774 | 0.8822 | 0.8920 | 0.8871 | 0.8819 | 0.8827 | 0.8779 | 0.8813 |
| RV_LV Ratio<1 | 0.8597 | 0.8606 | 0.862 | 0.8644 | 0.8619 | 0.8567 | 0.8676 | 0.8642 | 0.8644 |
| Chronic PE | 0.7304 | 0.7256 | 0.7233 | 0.7788 | 0.7664 | 0.7699 | 0.7234 | 0.7168 | 0.7342 |
| Acute&Chronic PE | 0.8453 | 0.8470 | 0.8228 | 0.8392 | 0.8396 | 0.8350 | 0.8405 | 0.8341 | 0.8367 |
| Mean AUC | 0.8830 | 0.8805 | 0.8785 | 0.8859 | 0.8807 | 0.8831 | 0.8773 | 0.8716 | 0.8751 |

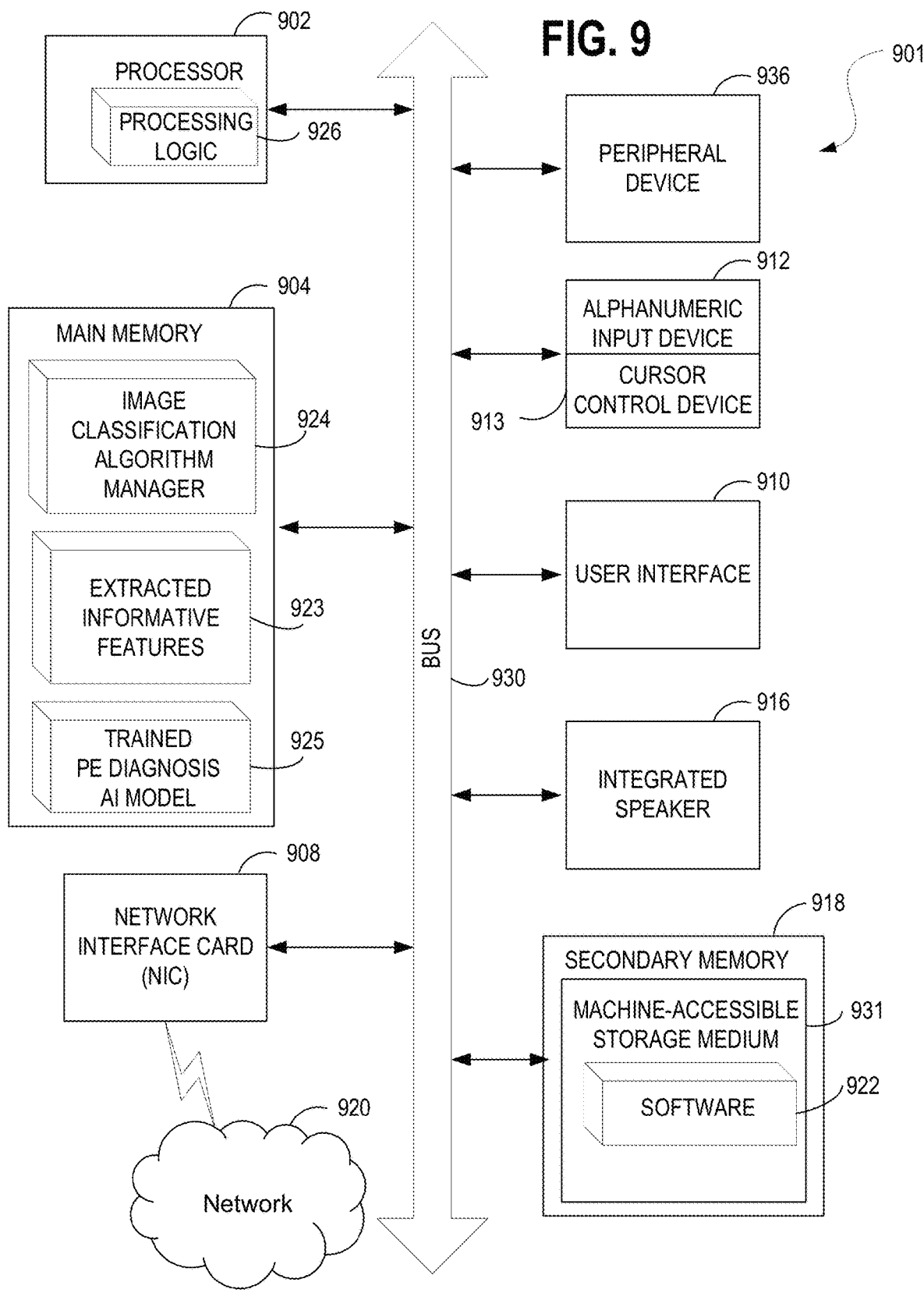

SYSTEMS, METHODS, AND APPARATUSES FOR SYSTEMATICALLY DETERMINING AN OPTIMAL APPROACH FOR THE COMPUTER-AIDED DIAGNOSIS OF A PULMONARY EMBOLISM

CLAIM OF PRIORITY

This non-provisional U.S. Utility patent application is related to, and claims priority to the U.S. Provisional Patent Application No. 63/244,183, filed on Sep. 14, 2021 entitled "Seeking an Optimal Approach for Computer-Aided Diagnosis of a Pulmonary Embolism," the entire contents of which are incorporated herein by reference as though set forth in full.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for systematically determining an optimal approach for the computer-aided diagnosis of a pulmonary embolism, in the context of processing of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Overfitting happens when a machine learning model has become too attuned to the data on which it was trained and therefore loses its applicability to any other dataset. A model is overfitted when it is so specific to the original data that trying to apply it to data collected in the future would result poor predictions and erroneous outcomes and therefore less-than-optimal decisions.

As is well understood, merely generating predictive output is not necessarily useful and could even prove to be counter productive, especially in the context of medical image diagnosis. What is needed is a reliable and robust methodology by which to generate optimal predictive outputs.

The present state of the art may therefore benefit from the systems, methods, and apparatuses for systematically determining an optimal approach for the computer-aided diagnosis of a pulmonary embolism, as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 2A presents Table 1 showing that ViT performs inferiorly compared with CNN for image-level PE classification, in accordance with described embodiments;

FIG. 3C depicts Table 3 which lists tabular results corresponding to the graphs set forth at FIGS. 3A and 3B, in accordance with described embodiments;

FIG. 5B depicts Table 4 which lists tabular results corresponding to the chart set forth at FIG. 5A, in accordance with described embodiments;

FIG. 6 presents Table 5 showing that the performance varies with pooling strategies for Multiple Instance Learning (MIL). Attention and Max Pooling (AMP) combines the output of Max Pooling (MP) and Attention Pooling (AP);

FIG. 9 illustrates a diagrammatic representation of a machine in the exemplary form of a computer system, in accordance with one embodiment.

DETAILED DESCRIPTION

Figure 1:
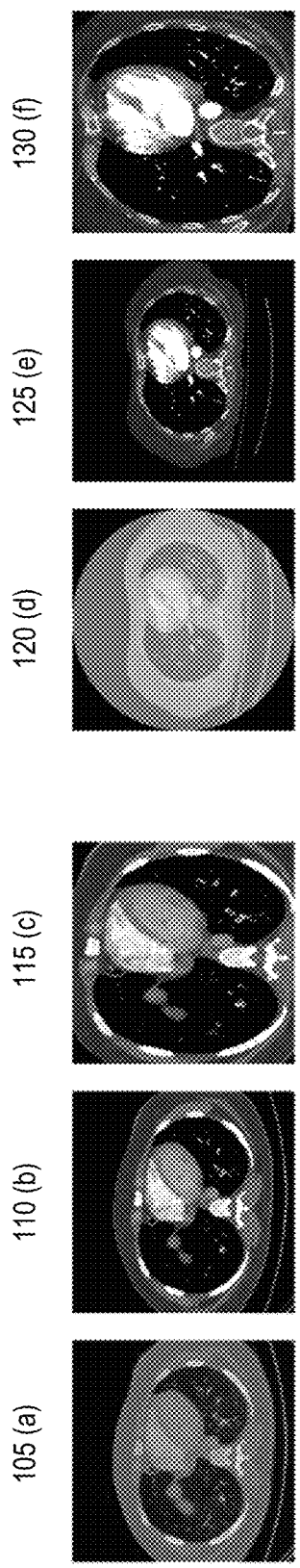
FIG. 1 depicts the pre-processing steps for image-level classification, in accordance with described embodiments.

Described herein are systems, methods, and apparatuses for systematically determining an optimal approach for the computer-aided diagnosis of a pulmonary embolism, in the context of medical imaging.

In the field of medical diagnosis, a Pulmonary embolism (PE) represents a thrombus (occasionally colloquially, and incorrectly, referred to as a "blood clot"), usually originating from a lower extremity or pelvic vein, that travels to the blood vessels in the lung, causing vascular obstruction. Pulmonary Embolisms cause more deaths than lung cancer, breast cancer, and colon cancer combined. The current test of choice for Pulmonary embolism diagnosis is a Computed Tomography Pulmonary Angiography (CTPA). However, studies have shown a 14% under-diagnosis and a 10% over-diagnosis with the use of CTPA.

Computer-aided diagnosis (CAD) has shown great potential for improving the imaging diagnosis of Pulmonary Embolisms. However, recent research in deep learning across academia and industry produced numerous architectures, various model initialization, and distinct learning paradigms, resulting in many competing approaches to CAD implementation in medical imaging producing great confusion in the CAD community. To address this confusion and develop an optimal approach, the following question needs to be addressed: "What deep learning architectures, model initialization, and learning paradigms should be used for CAD applications in medical imaging?"

To answer the question, extensive experiments were conducted with various deep learning methods applicable for Pulmonary Embolism diagnosis at both image and exam levels using a publicly available Pulmonary Embolism dataset.

Convolutional Neural Networks (CNNs) have been the default architectural choice for classification and segmentation in medical imaging. Nevertheless, transformers have proven to be powerful in Natural Language Processing (NLP), and have been quickly adopted for image analysis, leading to vision transformer (ViT). Therefore, to assess architecture performance, ViT was compared with ten (10) Convolutional Neural Network variants for classifying Pulmonary Embolisms. Regardless of the architecture, training deep models generally requires massive carefully labeled training datasets. However, it is often prohibitive to create such large annotated datasets in medical imaging; therefore, fine-tuning models from ImageNet has become the de facto standard. As a result, various models pre-trained on ImageNet were benchmarked against training from scratch.

Supervised learning is currently the dominant approach for classification and segmentation in medical imaging, which offers expert-level and sometimes even super-expert-level performance. Self-supervised learning (SSL) has recently garnered attention for its capacity to learn generalizable representations without requiring expert annotation. The idea is to pre-train models on pretext tasks and then fine-tune the pre-trained models to the target tasks. Fourteen (14) different SSL methods for PE diagnosis were evaluated. In contrast to Conventional Classification (CC), which predicts a label for each instance, Multiple Instance Learning (MIL) makes a single prediction for a bag of instances; that is, multiple instances belonging to the same "bag" are assigned a single label. Multiple Instance Learning is label efficient because only a single label is required for each exam, insomuch that a single exam is considered a "bag" of instances. Therefore, it is important to ascertain the effectiveness of Multiple Instance Learning for Pulmonary Embolism diagnosis at the exam level.

The innovations described herein therefore provide at least the following three contributions, as follows: Firstly, (1) the innovations offer a comprehensive analysis of competitive deep learning methods for Pulmonary Embolism diagnosis; Secondly, (2) the innovations offer extensive experiments that compare architectures, model initialization, and learning paradigms. And thirdly, (3) the innovations offer an optimal approach for detecting a Pulmonary Embolism, achieving an AUC gain of 0.2% and 1.05% at the image and exam levels, respectively, compared with the state-of-the-art performance.

FIG. 1 depicts the pre-processing steps for image-level classification, in accordance with described embodiments.

As shown here, sub-images at elements 110 and 120 (a,d) correspond to original CT images, sub-images at elements 110 and 125 (b,e) correspond to CT images after windowing, and sub-images at elements 115 and 130 (c,f) correspond to CT images after lung localization. For windowing, pixels above 450 HU and below −250 HU were clipped to 450 HU and −250 HU, respectively.

FIG. 2A presents Table 1 at element 201 showing that ViT performs inferiorly compared with CNN for image-level PE classification. For both architectures (ViT-B_32 and ViT-B_16), random initialization provides the worst performance. Both increasing the image size and reducing the patch size can enlarge the training set and therefore lead to an improved performance. Finally, similar to CNNs, initializing ViTs on ImageNet21k provided significant performance gain, indicating the usefulness of transfer learning.

Figure 2B:
FIG. 2B presents Table 2 showing that the features extracted by the models trained for image-level classification were helpful for exam-level classification, in accordance with described embodiments.

FIG. 2B presents Table 2 at element 202 showing that the features extracted by the models trained for image-level classification were helpful for exam-level classification. However, no model performed consistently best for all labels. Table 2 reports the mean AUC over 10 runs and bold the optimal results for each label. The Xception architecture achieved a significant improvement (p=5.34E-12) against the previous state of the art.

Materials:

The Radiological Society of North America (RSNA) Pulmonary Embolism Detection Challenge (RSPED) aims to advance computer-aided diagnosis for Pulmonary Embolism detection. The dataset consists of 7,279 CTPA exams, with a varying number of images in each exam, using an image size of 512×512 pixels. The test set was created by randomly sampling 1000 exams, leaving the remaining 6,279 exams to form the training set. Correspondingly, there are 1,542,144 and 248,480 images in the training and test sets, respectively. This dataset is annotated at both image and exam level; that is, each image has been annotated as having either a PE presence or a PE absence. Each exam has been annotated for an additional nine labels (refer to Table 2 as set forth at FIG. 2B).

Similar to the first place solution for this challenge, lung localization and windowing have been used as pre-processing steps. Lung localization removes the irrelevant tissues and keeps the region of interest in the images, whereas windowing highlights the pixel intensities within the range of [100, 700]. Additionally, the images are resized to 576×576 pixels.

More particularly, FIG. 1, illustrates these pre-processing steps in greater detail, showing the consideration of three (3) adjacent images from an exam as the 3-channel input of the model.

Methods—Image-Level Classification:

Image-level classification refers to determining the presence or absence of PE for each image. The configurations of supervised and self-supervised transfer learning are described in greater detail here.

Supervised Learning: The idea is to pre-train models on ImageNet with ground truth and then fine-tune the pre-trained models for PE diagnosis, ten different CNN architectures were examined (Refer to FIG. 3).

Extending upon and further customizing each of SeResNext50 and SeResNet50, a squeeze and excitation (SE) block was introduced into a specialized configuration of the Xception architecture (SeXception). These CNN architectures were pre-trained on ImageNet taken from PyTorch while SeXception was pre-trained on ImageNet.

Further explored was the usefulness of vision transformer (ViT), where the images are reshaped into a sequence of patches. Specifically, experiments were conducted with ViT-B_32 and ViT-B_16, utilizing 32×32 and 16×16 patches, respectively. Again, ViT architectures were pre-trained on ImageNet21k. Upscaling the image for a given patch size will effectively increase the number of patches, thereby enlarging the size of the training dataset; models are also trained on different sized images. Similarly, the number of patches increases with a decrease in the patch size.

Self-Supervised Learning (SSL): In self-supervised transfer learning, the model is pre-trained on ImageNet without ground truth and then fine-tuned for PE diagnosis. Self-supervised learning has gained attention recently and with the assistance of strong augmentation and comparing different contrastive losses, a model can learn meaningful information, even without annotations.

These architectures are first trained for a pretext task; for example, reconstructing the original image from its distorted version. Then the models are fine-tuned for a different task, in this particularly embodiment, PE detection.

Models were pre-trained through fourteen (14) different Self-Supervised Learning approaches, all of which used ResNet50 as the backbone.

Exam-Level Classification:

Apart from the image-level classification, the Radiological Society of North America (RSNA) Pulmonary Embolism Detection Challenge (RSPED) dataset also provides exam-level labels, in which only one label is assigned for each exam. For this task, the features extracted from the models trained for image-level PE classification were utilized and two learning paradigms were explored, as follows:

Conventional Classification (CC): First, all the extracted features were stacked together resulting in an N×M feature for each exam, where N and M denote the number of images per exam and the dimension of the image feature, respectively. However, as N varies from exam to exam, the feature was reshaped to K×M. For the sake of experiment, K was set equal to 192 and the features were then fed into a bidirectional Gated Recurrent Unit (GRU) followed by pooling and fully connected layers to predict exam-level labels.

Multiple Instance Learning (MIL): MIL is annotation efficient as it does not require annotation for each instance. An essential requirement for MIL is permutation invariant MIL pooling. Both max operators and attention-based operator are used as MIL pooling. A combination of these approaches were also subjected to experimentation. The MIL approach is innate for handling varying images (N) in the exams and does not require any reshaping operation as does Conventional Classification (CC). For Multiple Instance Learning (MIL) specifically, the same architecture as in Conventional Classification was exploited by replacing pooling with MIL pooling.

Figure 3A:
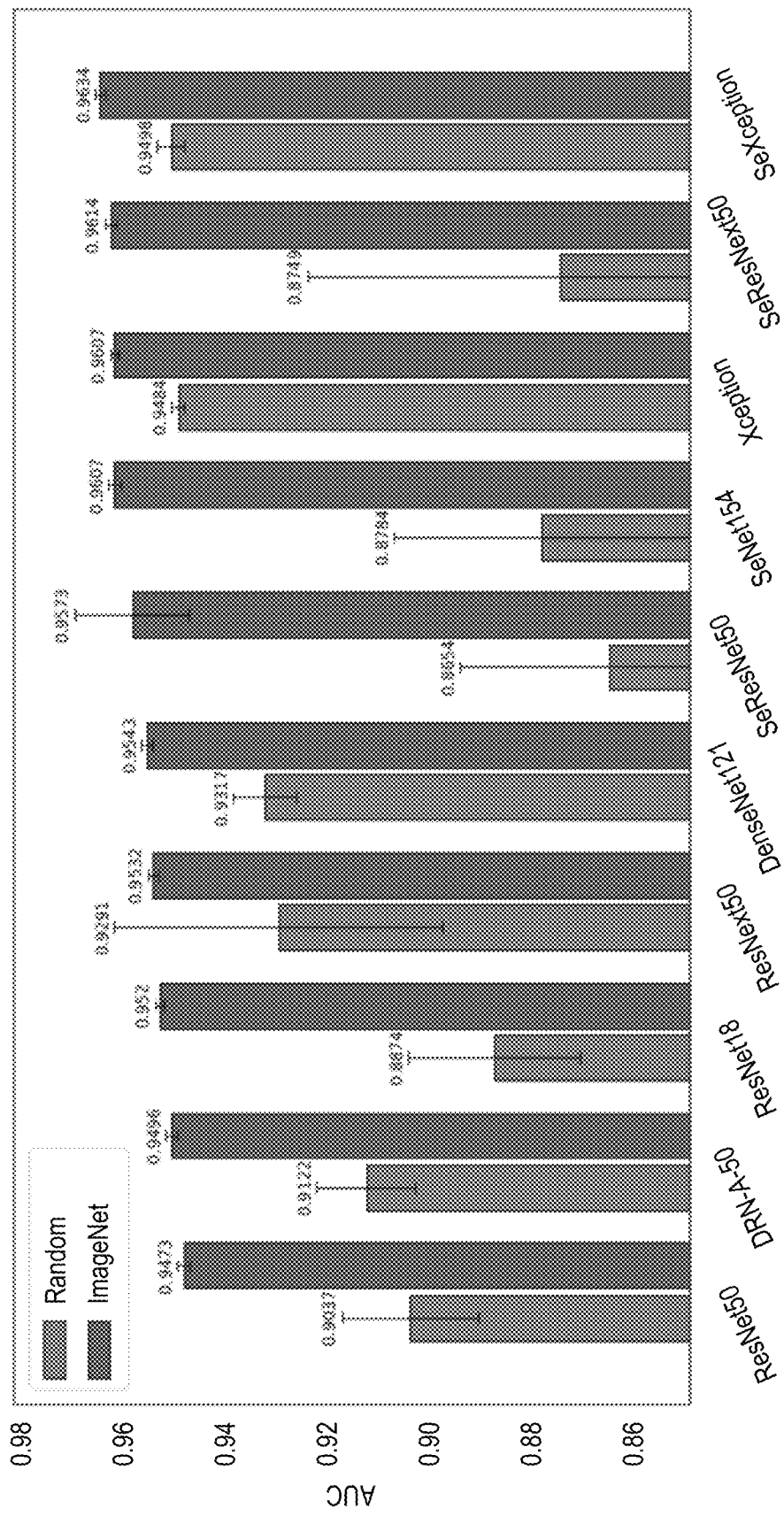
FIG. 3A depicts a graph showing that, for all 10 architectures, transfer learning outperformed random initialization in image-level PE classification, in spite of the pronounced difference between ImageNet and RSPED, in accordance with described embodiments.

FIG. 3A depicts a graph 301 showing that, for all 10 architectures, transfer learning outperformed random initialization in image-level PE classification, in spite of the pronounced difference between ImageNet and RSPED. Mean AUC and standard deviation over ten runs are further reported for each architecture. Compared with the previous state of the art, such as SeResNext50, the SeXception architecture achieved a significant improvement on the order of (p=1.68E-4).

Figure 3B:
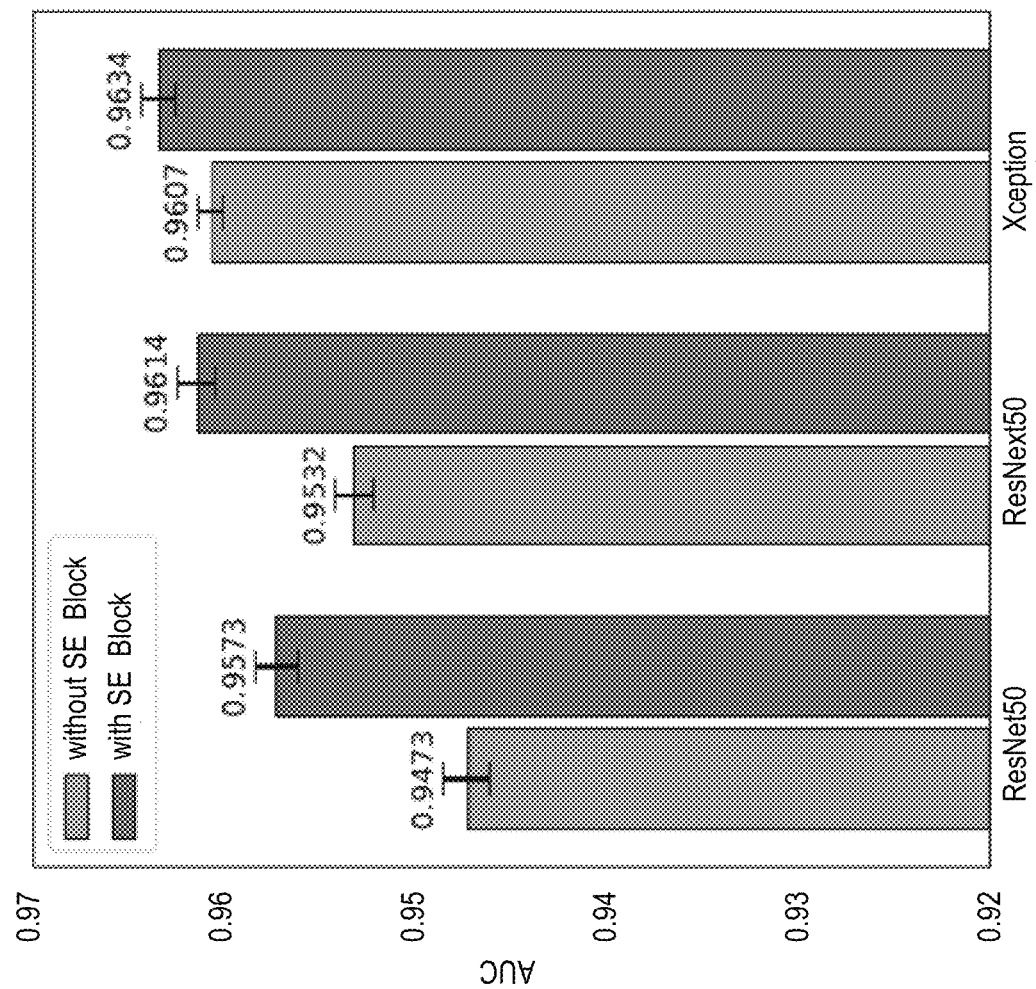
FIG. 3B depicts a graph showing an observed performance gain with the help of SE block. Note that, all the architectures under comparison were pre-trained from ImageNet, in accordance with described embodiments.

FIG. 3B depicts a graph 302 showing an observed performance gain with the help of SE block. Note that, all the architectures under comparison were pre-trained from ImageNet.

FIG. 3C depicts Table 3 at element 303 which lists tabular results corresponding to the graphs set forth at FIGS. 3A and 3B, in accordance with the described embodiments.

Figure 3D:
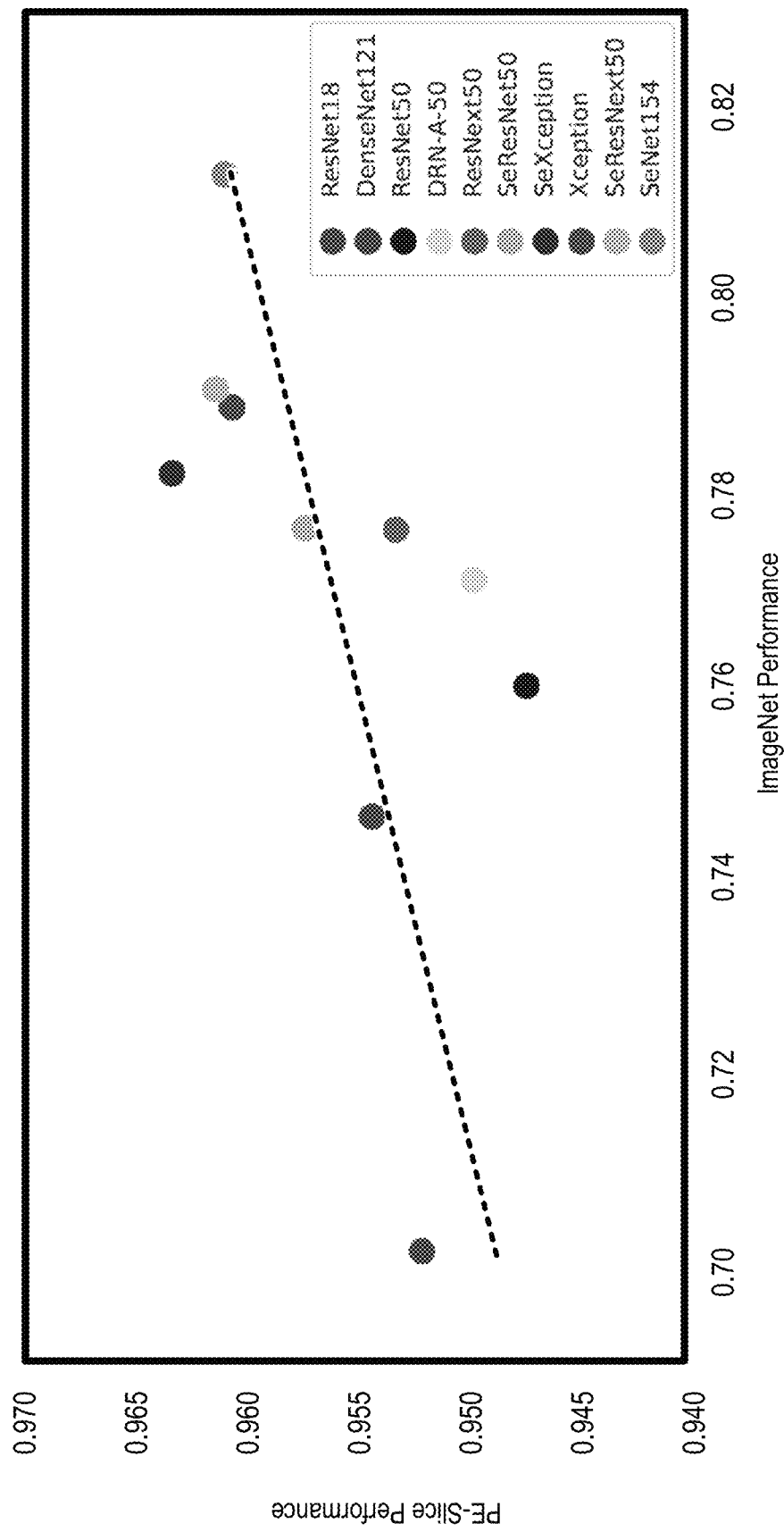
FIG. 3D illustrates a scatter plot showing a positive correlation between the results on ImageNet and RSPED, suggesting that the transfer learning performance could be inferred by ImageNet pre-training performance, in accordance with described embodiments.

FIG. 3D illustrates a scatter plot 304 showing a positive correlation between the results on ImageNet and RSPED (R=0.5914), suggesting that the transfer learning performance could be inferred by ImageNet pre-training performance.

Results and Discussion

Transfer learning significantly improves the performance of image-level classification despite the modality difference between the source and target datasets: As shown here at FIGS. 3A, 3B, and 3D, there is a significant performance gain for every pre-trained model compared with random initialization. There is also a positive correlation of 0.5914 between ImageNet performance and PE classification performance across different architectures (Refer to FIG. 3D), indicating that useful weights learned from ImageNet can be successfully transferred to the PE classification task, despite the modality difference between the two datasets.

Squeeze and excitation (SE) block enhances CNN performance: Despite fewer parameters compared with many other architectures, SeXception provides an optimal average AUC of 0.9634. SE block enables an architecture to extract informative features by fusing spatial and channel-wise information. Thus, the SE block has led to performance improvements from ResNet50 to SeResNet50, ResNext50 to SeResNext50 and from Xception to SeXception (Refer to FIG. 3B).

Figure 4:
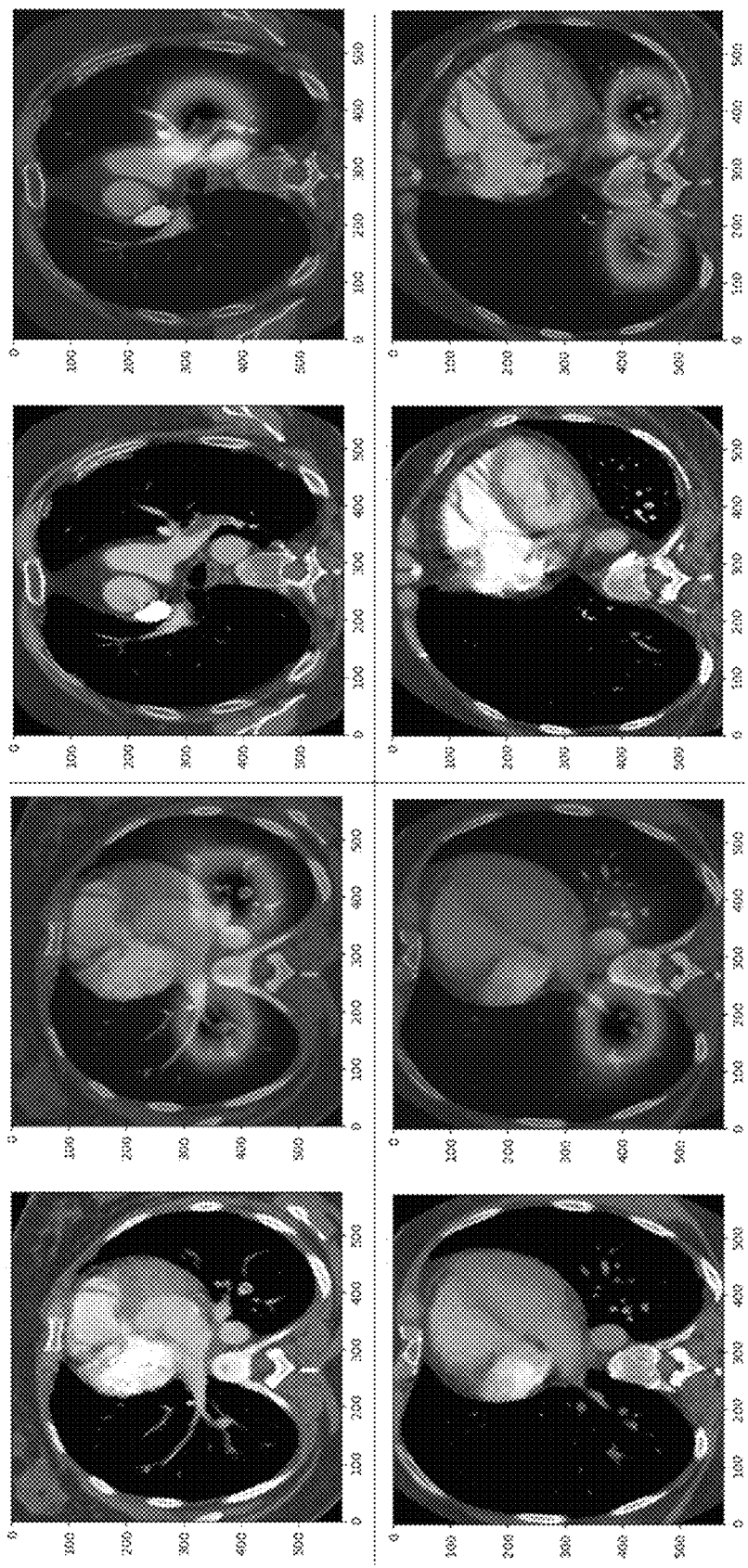
FIG. 4 illustrates the SeXception attention map highlighted the potential PE location in the image using Grad-Cam++, in accordance with described embodiments.

FIG. 4 illustrates the SeXception attention map highlighted the potential PE location in the image using GradCam++. Specifically, with the help of GradCam++, the attention map of SeXception was visualized, resulting in the best performing architecture.

As shown in FIG. 4, the attention map can successfully highlight the potential PE location in the image.

Figure 5A:
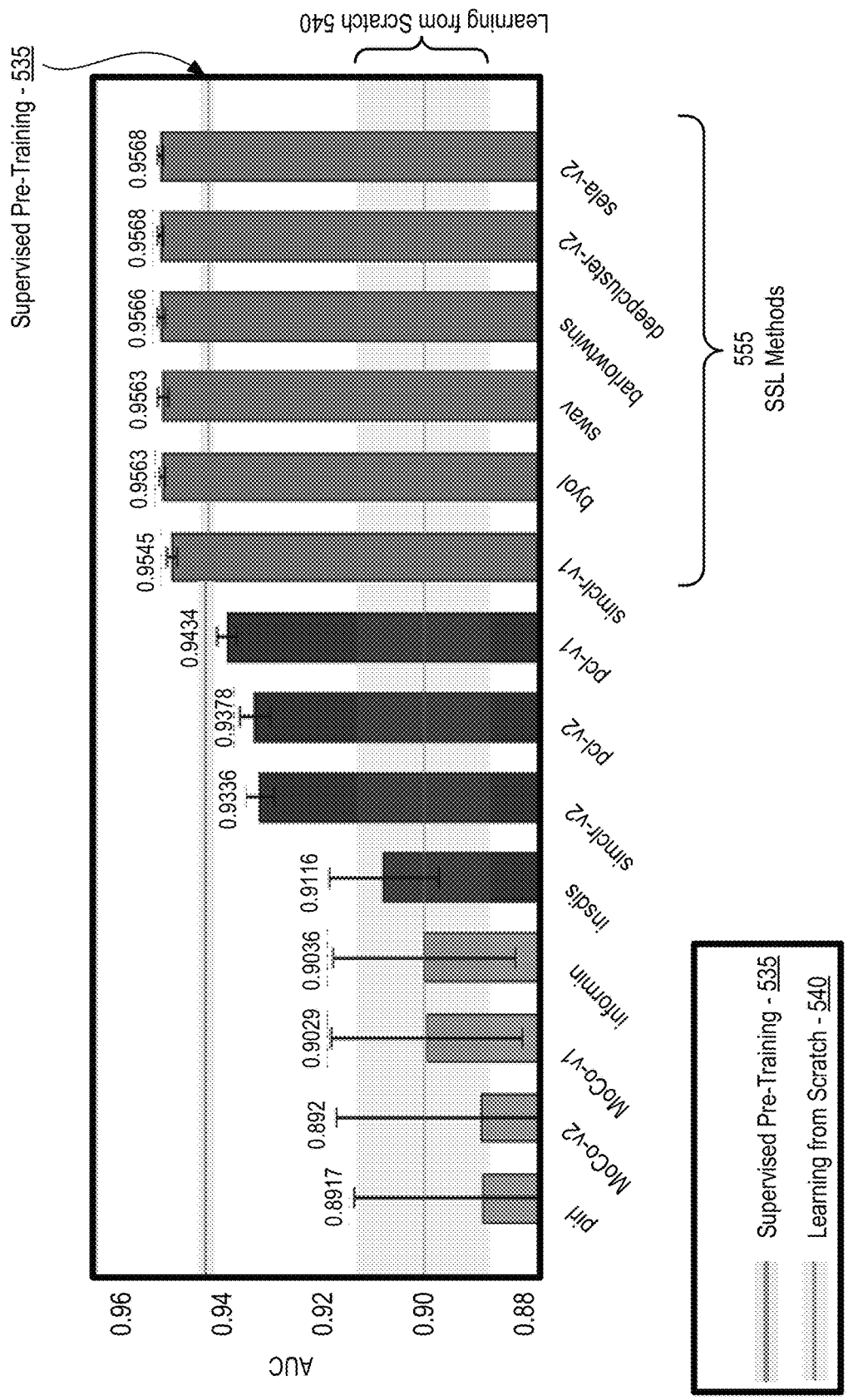
FIG. 5A depicts a chart showing how self-supervised pre-training extracted more transferable features compared with supervised pre-training, in accordance with described embodiments.

FIG. 5A depicts a chart 500 showing how self-supervised pre-training extracted more transferable features compared with supervised pre-training. The upper and lower lines represent supervised pre-training and learning from scratch with standard deviation (shaded), respectively. As shown here, six (6) out of the fourteen (14) SSL methods 555 outperformed the supervised pre-training. All the reported methods had ResNet50 as the backbone.

FIG. 5B depicts Table 4 at element 501 which lists tabular results corresponding to the chart set forth at FIG. 5A, in accordance with the described embodiments.

FIG. 6 presents Table 5 at element 600 showing that the performance varies with pooling strategies for Multiple Instance Learning (MIL). Attention and Max Pooling (AMP) combines the output of Max Pooling (MP) and Attention Pooling (AP). Multiple Instance Learning utilized the feature extracted by the model trained for image-level PE classification. For all three architectures, the best mean AUC is obtained by AMP, highlighting the importance of combining AP and MP.

Transfer learning with a self-supervised paradigm produces better results than its supervised counterparts: As summarized by FIG. 5A, SeLav2 and DeepCluster-v2 achieved the best AUC of 0.9568, followed by Barlow Twins, with fully six (6) out of the fourteen (14) SSL models performing better than supervised pre-trained ResNet50.

CNNs have better performance than ViTs: As shown in Table 1, as depicted at FIG. 2A, random initialization provides a significantly lower performance than ImageNet pre-training. The best AUC of 0.9179 is obtained by ViT-B_16 with image size 576×576 and ImageNet21k initialization. However, this performance is inferior to the optimal CNN architecture (SeXception) by a significant margin of approximately 4%. This result is attributable to the absence of convolutional filters in ViTs.

Conventional classification (CC) marginally outperforms MIL: The results of conventional classification for exam-level predictions are summarized in Table 2 as depicted at FIG. 2B. Although SeXception performed optimally for image-level classification (Refer to FIGS. 3A and 3B), the same is not true for exam-level classification. There is no architecture that performs optimally across all labels, but overall, Xception shows the best AUC across nine labels. The results of Multiple Instance Learning (MIL) for exam-level predictions are summarized in Table 5 as depicted at FIG. 6. Xception achieved the best AUC with a combination of attention and max pooling. Similar to conventional classification approach, no single Multiple Instance Learning method performs optimally for all labels. However, Xception shows the best mean AUC of 0.8859 with Attention and Max Pooling across all labels. Furthermore, the AUC for MIL is marginally lower than CC (0.8859 vs. 0.8912) but the later requires additional prepossessing steps. More importantly, MIL provides a more flexible approach and can easily handle varying number of images per exam. Based on result #3, the performance of exam-level classification may be improved by incorporating the features from SSL methods.

Seeking the optimal approach: The existing first place solution utilizes SeResNext50 for image-level and CC for exam-level classification. The optimal approach is described herein which outperforms prior solutions. Specifically, this optimal approach achieved an AUC gain of 0.2% and 1.05% for image-level and exam-level PE classification, respectively, through the practice of the disclosed embodiments. Based on rigorous analysis, the optimal architectures for the tasks of image-level and exam-level classification were determined to be SeXception and Xception.

Backbone Architectures:

Experiments conducted with other backbones (Refer to FIGS. 3A and 3B) may further explore if SSL models outperform other supervised counterparts as well.

ResNet18 and Resnet50: One way to improve an architecture is to add more layers and make it deeper. Unfortunately, increasing the depth of a network do not work simply by stacking layers together. As a result, it can introduce the problem called vanishing gradient. Moreover, the performance might get saturated or decreased over time. The main idea behind ResNet is to have identity shortcut connection which skips one or more layer. Stacking layers should not decrease the performance of the network. The residual block allows the network to have identity mapping connections which prevents from vanishing gradient. Several versions of ResNet models have been presented, including ResNet18, ResNet34, ResNet50 and ResNet101. The numbers indicate how many layers exist within the architecture. The more layers represent deeper network and the trainable parameters increase accordingly.

ResNext50: In ResNext50, a new dimension C is introduced which is called Cardinality. The cardinality controls the size of the set of transformations addition to the dimensions of depth and width. Increasing cardinality is considered more effective than going deeper or wider in terms of layers. This architecture was used in the ILSVRC 2016 classification competition and secured the 2nd place. Comparing to ResNet50, ResNext50 has similar numbers of parameters for training and can boost the performance. Stated differently, ResNext50 could achieve almost equivalent performance to ResNet101 although ResNet101 has deeper layers.

DenseNet121: Increasing the depth of a network results in performance improvement. However, the problem arise when the network is too deep. As a result, the path between input and output becomes too long which introduces the popular issue called vanishing gradient. DenseNets simply redesign the connectivity pattern of the network so that the maximum information is flown. The main idea is to connect every layer directly with each other in a feed-forward fashion. For each layer, the feature-maps of all preceding layers are used as inputs, and its own feature-maps are used as inputs into all subsequent layers. The advantages of using DenseNet is that they alleviate the vanishing-gradient problem, strengthen feature propagation, encourage feature reuse, and substantially reduce the number of parameters.

Xception: The Xception network architecture was built on top of Inception-v3. It is also known as an extreme version of Inception module. With a modified depthwise separable convolution, it is even better than Inception-v3. The original depthwise separable convolution is to do depthwise convolution first and then a pointwise convolution. Here, Depthwise convolution is the channel-wise spatial convolution and pointwise convolution is the 1×1 convolution to change the dimension. This strategy is modified for Xception architecture. In Xception, the depthwise separable convolution performs 1×1 pointwise convolution first and then channel-wise spatial convolution. Moreover, Xception and Inception-v3 has the same number of parameters. The Xception architecture slightly outperforms Inception-v3 on the ImageNet dataset and significantly outperforms Inception-v3 on a larger image classification dataset including 350 million images and 17,000 classes.

DRN-A-50: Usually in image classification task the Convolutional Neural Network progressively reduces resolution until the image is represented by tiny feature-maps in which the spatial structure of the scene is not quite visible. This kind of spatial structure loss can hamper image classification accuracy as well as complicate the transfer of the model to a downstream task. This architecture introduces dilation which increases the resolutions of the feature-maps with-out reducing the receptive field of individual neurons. Dilated residual networks (DRNs) can outperform their non-dilated counterparts in image classification task. This strategy does not increase the model's depth or the complexity. As a result the number of parameters stays the same comparing to the counterparts.

SeNet154: The convolution operator enables networks to construct informative features by fusing both spatial and channel-wise information within local receptive fields at each layer. This work focused on a channel-wise relationship and proposed a novel architectural unit called Squeeze-and-Excitation (SE) block. This SE block adaptively re-calibrates channel-wise feature responses by explicitly modeling inter-dependencies between channels. These blocks can also be stacked together to form a network architecture (SeNet154) and generalize extremely effectively across different datasets. SeNet154 is one of the superior models used in ILSVRC 2017 Image Classification Challenge and won the first place.

SeResNet50, SeResNext50 and SeXception: The structure of the Squeeze-and-Excitation (SE) block can be added to any state-of-the-art architectures by replacing components with their SE counterparts. SE blocks are also computationally lightweight and impose only a slight increase in model complexity and computational burden. SE blocks were added to ResNet50 and ResNext50 model to design the new version. The pre-trained weights for SeResNet50 and SeResNext50 already exists where SeXception is not present. By adding SE blocks, a highly specialized and customized variant of the SeXception architecture was created and trained on ImageNet dataset to achieve the pre-trained weights. Subsequently, the pre-trained weights were successfully applied to specialized transfer learning schemes.

Self Supervised Methods:

InsDis: InsDis trains a non-parametric classifier to distinguish between individual instance classes based on NCE (noise-contrastive estimation). Moreover, each instance of an image works as a distinct class of its own for the classier. InsDis also introduces a feature memory bank to maintain a large number of noise samples (referring to negative samples). This helps to avoid exhaustive feature computing.

MoCo-v1 and MoCo-v2: MoCo-v1 uses data augmentation to create two views of a same image X referring as positive samples. Similar to InsDis, images other than X are defined as negative samples and they are stored in a memory bank. Moreover, to ensure the consistency of negative samples, a momentum encoder is introduced as the samples evolve during the training process. Basically, the methodology aims to increase the similarity between positive samples while decreasing the similarity between negative samples. On the other hand, MoCo-v2 works similarly adding non-linear projection head, few more augmentations, cosine decay schedule, and a longer training time.

SimCLR-v1 and SimCLR-v2: The key idea of SimCLR-v1 is similar to MoCo yet proposing independently. Here, SimCLR-v1 is trained in an end-to-end fashion with larger batch sizes instead of using special network architectures (a momentum encoder) or a memory bank. Within each batch, the negative samples are generated on the fly. However, SimCLR-v2 optimizes the previous version by increasing the capacity of the projection head and incorporating the memory mechanism from MoCo to provide more meaningful negative samples.

BYOL: MoCo and SimCLR methods mainly relies on a large number of negative samples and they require either a large memory bank or a large batch size. On the other hand, BYOL replaces the use of negative pairs by adding an online encoder, target encoder and a predictor after the projector in the online encoder. Both the target encoder and the online encoder computes features. The key idea is to maximize the agreement between target encoder's features and prediction from the online encoder. To prevent the collapsing problem, the target encoder is updated by the momentum mechanism.

PIRL: Both InsDis and MoCo takes the advantage of using instance discrimination. However, PIRL adapts the Jigsaw and Rotation as proxy tasks. Here, the positive samples are generated by applying Jigsaw shuffling or rotating by {0-degrees, 90-degrees, 180-degrees, 270-degrees}. Following InsDis, PIRL uses Noise-Contrastive estimation (NCE) as loss function and a memory bank.

DeepCluster-v2: DeepCluster uses two phases to learn features. First, it uses self-labeling, where pseudo labels are generated by clustering data points using prior representation yielding cluster indexes for each sample. Secondly, it uses feature-learning, where each sample's cluster index is used as a classification target to train a model. Until the model is converged, the two phases mentioned above is performed repeatedly. The DeepCluster-v2 minimizes the distance between each sample and the corresponding cluster centroid. DeepCluster-v2 also uses stronger data augmentation, MLP projection head, cosine decay schedule, and multi-cropping to improve the representation learning.

SeLa-v2: SeLa also requires two-phase training (e.g., self-labeling and feature-learning). SeLa focuses on self-labeling as an optimal transport problem and solves it using Sinkhorn-Knopp algorithm. SeLa-v2 also uses stronger data augmentation, MLP projection head, cosine decay schedule, and multi-cropping to improve the representation learning.

PCL-v1 and PCL-v2: PCL-v1 aims to bridge contrastive learning with clustering. PCL-v1 adopts the same architecture as MoCo, including an online encoder and a momentum encoder. Following clustering-based feature learning, PLC-v1 also uses two phases (self-labeling and feature-learning). The features obtained from the momentum encoder are clustered in self-labeling phase. On the other hand, PCL-v1 generalizes the NCE loss to ProtoNCE loss instead of classifying the cluster index with regular cross-entropy. This was done in PCL-v2 as an improvement step.

SwAV: SwAV uses both contrastive learning as well as clustering techniques. For each data sample, SwAV calculates cluster assignments (codes) with the help the Sinkhorn-Knopp algorithm. Moreover, SwAV works online performing assignments at the batch level instead of epoch level.

InfoMin: InfoMin suggested that for contrastive learning, the optimal views depend upon the downstream task. For optimal selection, the mutual information between the views should be minimized while preserving the task-specific information.

Barlow Twins: The Barlow Twins consists of two identical networks fed with the two distorted versions of the input sample. The network is trained such that the cross-correlation matrix between the two resultant embedding vectors is close to the identity. A regularization term is also included in the objective function to minimize redundancy between embedding vectors' components.

Figure 7:
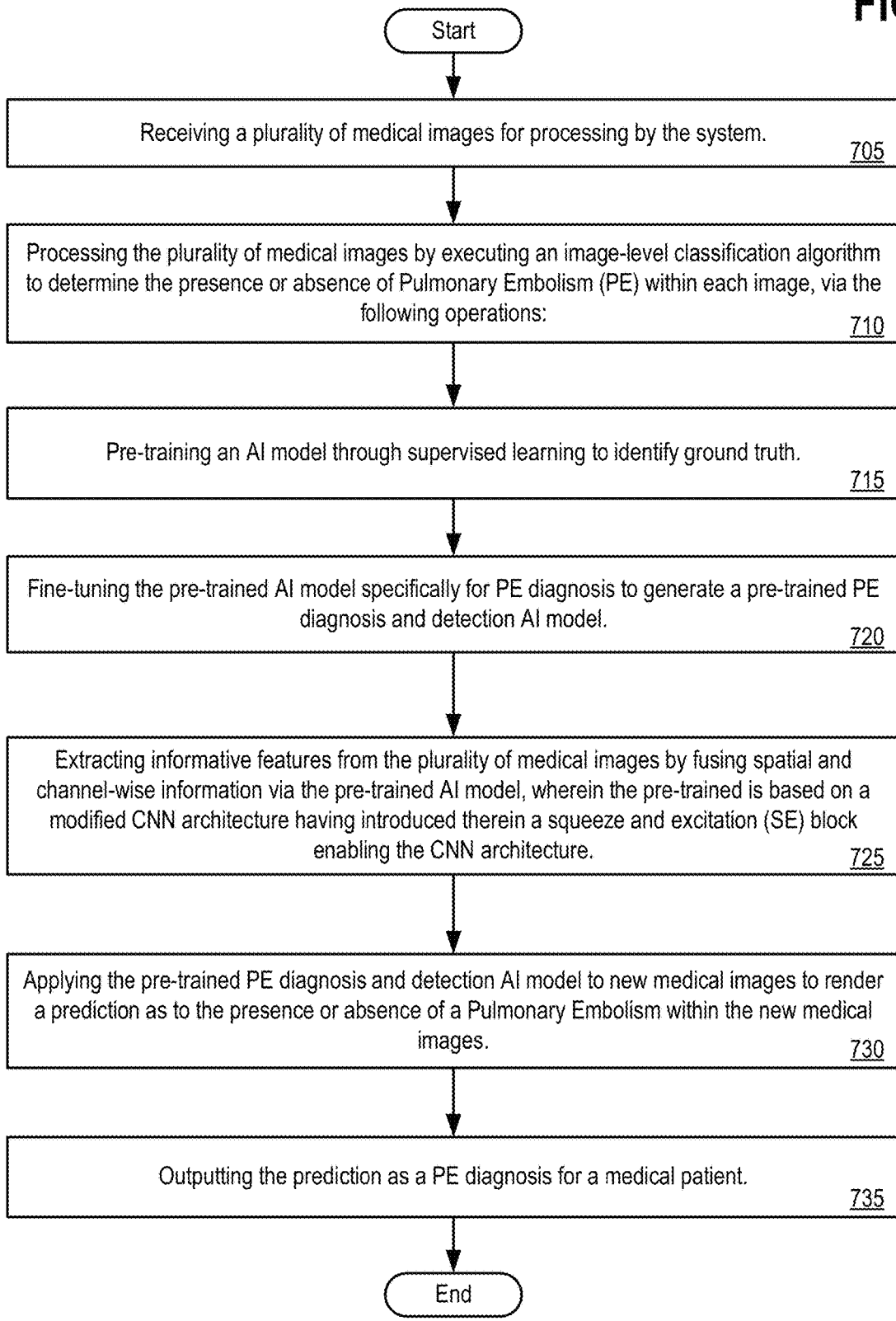
FIG. 7 depicts a flow diagram illustrating a method for systematically determining an optimal approach for the computer-aided diagnosis of a pulmonary embolism, in the context of processing of medical imaging, in accordance with disclosed embodiments.

FIG. 7 depicts a flow diagram illustrating a method 700 for systematically determining an optimal approach for the computer-aided diagnosis of a pulmonary embolism, in the context of processing of medical imaging, in accordance with disclosed embodiments. Method 700 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 801 (see FIG. 8) and the machine 901 (see FIG. 9) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 700 depicted at FIG. 7, there is a method performed by a system specially configured for systematically determining the optimal approach for the computer-aided diagnosis of a pulmonary embolism. Such a system may be configured with at least a processor and a memory to execute specialized instructions which cause the system to perform the following operations:

At block 705, processing logic of such a system receives a plurality of medical images for processing by the system.

At block 710, processing logic processes the plurality of medical images by executing an image-level classification algorithm to determine the presence or absence of Pulmonary Embolism (PE) within each image by performing the following operations:

At block 715, processing logic pre-trains an AI model through supervised learning to identify ground truth.

At block 720, processing logic fine-tunes the pre-trained AI model specifically for PE diagnosis to generate a pre-trained PE diagnosis and detection AI model.

At block 725, processing logic extracts informative features from the plurality of medical images by fusing spatial and channel-wise information via the pre-trained AI model, in which the pre-trained is based on a modified CNN architecture having introduced therein a squeeze and excitation (SE) block enabling the CNN architecture.

At block 730, processing logic applies the pre-trained PE diagnosis and detection AI model to new medical images to render a prediction as to the presence or absence of a Pulmonary Embolism within the new medical images.

At block 735, processing logic outputs the prediction as a PE diagnosis for a medical patient.

According to another embodiment of method 700, the new medical images constitute no part of any training set of medical images utilized to pre-train or fine-tune the AI model and have not been encountered by the pre-trained AI model prior to applying the pre-trained PE diagnosis and detection AI model to the new medical images.

According to another embodiment, method 700 further includes: pre-training a vision transformer (ViT) architecture with a training image dataset; and up scaling each image in the training image dataset for a given patch size to increase the number of patches resulting in an enlarged size of the training image dataset.

According to another embodiment, method 700 further includes: pre-training an AI model using different sized images generated from the upscaling of each image in the training image dataset for a given patch size.

According to another embodiment of method 700, applying the pre-trained PE diagnosis and detection AI model to new medical images to render a prediction as to the presence or absence of a Pulmonary Embolism within the new medical images includes: applying an image-level classification procedure individually to each one of the new medical images to determine, for each one of the new medical images, either the Pulmonary Embolism is present within the respective one of the new medical images or the Pulmonary Embolism is absent from the respective one of the new medical images.

According to another embodiment of method 700, pre-training an AI model through supervised learning to identify ground truth includes applying pre-training via self-supervised learning using a publically available dataset having training images annotated as either PE presence or PE absence.

According to another embodiment of method 700, the computer-implemented method further enlarges the training dataset's size beyond a received size for the training dataset by: (i) reshaping each of the plurality of images of the training dataset into a sequence of patches; and (ii) upscaling a corresponding image for each patch within the sequence of patches to generate an increased quantity of patches.

According to another embodiment of method 700, pre-training the AI model through supervised learning to identify ground truth includes executing instructions for pre-training the AI model through supervised learning using the increased quantity of patches as an enlarged training dataset.

According to a particular embodiment, there is a non-transitory computer-readable storage medium having instructions stored thereupon that, when executed by a system having at least a processor and a memory therein, the instructions cause the system to perform operations including: receiving a plurality of medical images; processing the plurality of medical images by executing an image-level classification algorithm to determine the presence or absence of a Pulmonary Embolism (PE) within each image; pre-training an AI model through supervised learning to identify ground truth; fine-tuning the pre-trained AI model specifically for PE diagnosis to generate a pre-trained PE diagnosis and detection AI model; wherein the pre-trained AI model is based on a modified CNN architecture having introduced therein a squeeze and excitation (SE) block enabling the CNN architecture to extract informative features from the plurality of medical images by fusing spatial and channel-wise information; applying the pre-trained PE diagnosis and detection AI model to new medical images to render a prediction as to the presence or absence of the Pulmonary Embolism within the new medical images; and outputting the prediction as a PE diagnosis for a medical patient.

Figure 8:
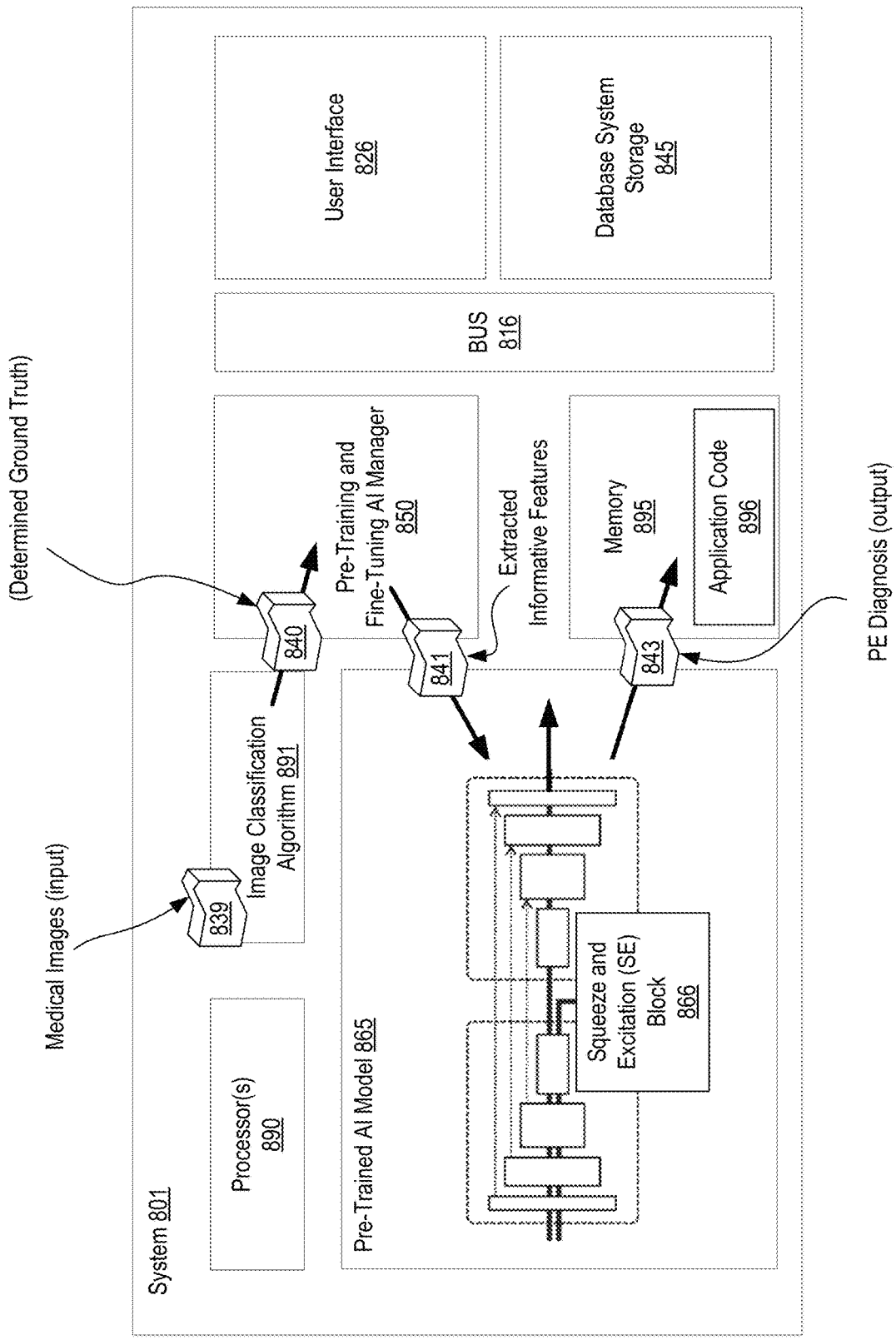
FIG. 8 shows a diagrammatic representation of a system within which embodiments may operate, be installed, integrated, or configured.

FIG. 8 shows a diagrammatic representation of a system 801 within which embodiments may operate, be installed, integrated, or configured. In accordance with one embodiment, there is a system 801 having at least a processor 890 and a memory 895 therein to execute implementing application code 896. Such a system 801 may communicatively interface with and cooperatively execute with the benefit of remote systems, such as a user device sending instructions and data, a user device to receive as an output from the system 801 a pre-trained diagnosis AI model having therein squeeze and execution block (SE block) 866 specially configured within a CNN base architecture.

According to the depicted embodiment, the system 801, includes a processor 890 and the memory 895 to execute instructions at the system 801. The system 801 as depicted here is specifically customized and configured to systematically determine an optimal approach for the computer-aided diagnosis of a pulmonary embolism, in the context of processing of medical imaging, in which a trained PE diagnosis model is rendered and available for use and execution for the processing of diagnosing the absence or presence of a PE within medical imaging input data.

According to a particular embodiment, system 801 is specially configured to receive a plurality of medical images as input 839; process the plurality of medical images 839 by executing an image-level classification algorithm 891 to determine the presence or absence of Pulmonary Embolism (PE) within each image as the PE diagnosis output 843. The system is further specially configured to pre-train an AI model 865 through supervised learning to identify ground truth 840; fine-tune the pre-trained AI model specifically for PE diagnosis to generate a pre-trained PE diagnosis 843 and detection AI model; in which the pre-trained AI model 865 is based on a modified CNN architecture having introduced therein a squeeze and excitation (SE) block 866 enabling the CNN architecture to extract informative features 841 from the plurality of medical images by fusing spatial and channel-wise information. The system 801 further applies the pre-trained PE diagnosis and detection AI model to new medical images to render a prediction as to the presence or absence of a Pulmonary Embolism within the new medical images; and provides as output 843, the prediction as a PE diagnosis for a medical patient.

As shown, the pre-training and fine-tuning AI manager 850 may perform pre-training to extract the informative features 841 which are then provided to or consumed by the trained AI model used to generate the PE diagnosis as output 843.

According to another embodiment of the system 801, a user interface 826 communicably interfaces with a user client device remote from the system and communicatively interfaces with the system via a public Internet.

Bus 816 interfaces the various components of the system 801 amongst each other, with any other peripheral(s) of the system 801, and with external components such as external network elements, other machines, client devices, cloud computing services, etc. Communications may further include communicating with external devices via a network interface over a LAN, WAN, or the public Internet.

FIG. 9 illustrates a diagrammatic representation of a machine 901 in the exemplary form of a computer system, in accordance with one embodiment, within which a set of instructions, for causing the machine/computer system to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 901 includes a processor 902, a main memory 904 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 918 (e.g., a persistent storage device including hard disk drives and a persistent database and/or a multi-tenant database implementation), which communicate with each other via a bus 930. Main memory 904 includes an image classification algorithm manager 924 for performing and executing image classification operations on received input images, which are provided to an extractor to extract and store extracted informative features 923, in support of pre-training and rendering the trained PE diagnosis AI model 925 for execution which is then operable to receive medical input images that did not form any part of the AI model training or pre-training and diagnose whether or not the medical image in question has or does not have a pulmonary embolism (PE) present within the image, within the context of processing medical imaging in support of the methodologies and techniques described herein. Main memory 904 and its sub-elements are further operable in conjunction with processing logic 926 and processor 902 to perform the methodologies discussed herein.

Processor 902 represents one or more specialized and specifically configured processing devices such as a microprocessor, central processing unit, or the like. More particularly, the processor 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 902 may also be one or more special-purpose processing devices such as an application-specific integrated circuit (ASIC), a field programmable gate array (FPGA), a digital signal processor (DSP), network processor, or the like. Processor 902 is configured to execute the processing logic 926 for performing the operations and functionality which is discussed herein.

The computer system 901 may further include a network interface card 908. The computer system 901 also may include a user interface 910 (such as a video display unit, a liquid crystal display, etc.), an alphanumeric input device 912 (e.g., a keyboard), a cursor control device 913 (e.g., a mouse), and a signal generation device 916 (e.g., an integrated speaker). The computer system 901 may further include peripheral device 936 (e.g., wireless or wired communication devices, memory devices, storage devices, audio processing devices, video processing devices, etc.).

The secondary memory 918 may include a non-transitory machine-readable storage medium or a non-transitory computer readable storage medium or a non-transitory machine-accessible storage medium 931 on which is stored one or more sets of instructions (e.g., software 922) embodying any one or more of the methodologies or functions described herein. The software 922 may also reside, completely or at least partially, within the main memory 904 and/or within the processor 902 during execution thereof by the computer system 901, the main memory 904 and the processor 902 also constituting machine-readable storage media. The software 922 may further be transmitted or received over a network 920 via the network interface card 908.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:
a memory to store instructions;
a processor to execute the instructions stored in the memory;
wherein the system is specially configured to:
receive a plurality of medical images;
process the plurality of medical images by executing an image-level classification algorithm to determine the presence or absence of Pulmonary Embolism (PE) within each image;
pre-train an AI model through supervised learning to identify ground truth;
fine-tune the pre-trained AI model specifically for PE diagnosis to generate a pre-trained PE diagnosis and detection AI model;
wherein the pre-trained AI model is based on a modified CNN architecture having introduced therein a squeeze and excitation (SE) block enabling the CNN architecture to extract informative features from the plurality of medical images by fusing spatial and channel-wise information;
apply the pre-trained PE diagnosis and detection AI model to new medical images to render a prediction as to the presence or absence of a Pulmonary Embolism within the new medical images; and
output the prediction as a PE diagnosis for a medical patient.

2. The system of claim 1, wherein the new medical images constitute no part of any training set of medical images utilized to pre-train or fine-tune the AI model and have not been encountered by the pre-trained AI model prior to applying the pre-trained PE diagnosis and detection AI model to the new medical images.

3. The system of claim 1, wherein the system is further specially configured to:
pre-train a vision transformer (ViT) architecture with a training image dataset; and
upscale each image in the training image dataset for a given patch size to increase the number of patches resulting in an enlarged size of the training image dataset.

4. The system of claim 3, wherein the system is further specially configured to:
pre-train an AI model using different sized images generated from the upscaling of each image in the training image dataset for a given patch size.

5. The system of claim 1, wherein applying the pre-trained PE diagnosis and detection AI model to new medical images to render a prediction as to the presence or absence of a Pulmonary Embolism within the new medical images comprises:
applying an image-level classification procedure individually to each one of the new medical images to determine, for each one of the new medical images, either the Pulmonary Embolism is present within the respective one of the new medical images or the Pulmonary Embolism is absent from the respective one of the new medical images.

6. The system of claim 1, wherein pre-training an AI model through supervised learning to identify ground truth comprises applying pre-training via self-supervised learning using a publically available dataset having training images annotated as either PE presence or PE absence.

7. The system of claim 1, wherein the system to receive a plurality of medical images comprises executing instructions for receiving a training dataset having included therein the plurality of medical images;
wherein the system is further specially configured to enlarge the training dataset's size beyond a received size for the training dataset by:
reshaping each of the plurality of images of the training dataset into a sequence of patches;
upscaling a corresponding image for each patch within the sequence of patches to generate an increased quantity of patches; and
wherein the system to pre-train the AI model through supervised learning to identify ground truth comprises the system executing instructions for pre-training the AI model through supervised learning using the increased quantity of patches as an enlarged training dataset.

8. A computer-implemented method performed by a system having at least a processor and a memory therein, wherein the computer-implemented method comprises:
executing instructions via the processor of the system for receiving a plurality of medical images at a receive interface of the system;
executing instructions via the processor of the system for processing the plurality of medical images by executing an image-level classification algorithm to determine the presence or absence of a Pulmonary Embolism (PE) within each image;
pre-training an AI model through supervised learning to identify ground truth;
fine-tuning the pre-trained AI model specifically for PE diagnosis to generate a pre-trained PE diagnosis and detection AI model;
wherein the pre-trained AI model is based on a modified CNN architecture having introduced therein a squeeze and excitation (SE) block enabling the CNN architecture to extract informative features from the plurality of medical images by fusing spatial and channel-wise information;
applying the pre-trained PE diagnosis and detection AI model to new medical images to render a prediction as to the presence or absence of the Pulmonary Embolism within the new medical images; and
outputting the prediction as a PE diagnosis for a medical patient.

9. The computer-implemented method of claim 8, wherein the new medical images constitute no part of any training set of medical images utilized to pre-train or fine-tune the AI model and have not been encountered by the pre-trained AI model prior to applying the pre-trained PE diagnosis and detection AI model to the new medical images.

10. The computer-implemented method of claim 8, further comprising:
pre-training a vision transformer (ViT) architecture with a training image dataset; and
upscaling each image in the training image dataset for a given patch size to increase the number of patches resulting in an enlarged size of the training image dataset.

11. The computer-implemented method of claim 10, further comprising:
pre-training an AI model using different sized images generated from the upscaling of each image in the training image dataset for a given patch size.

12. The computer-implemented method of claim 8, wherein applying the pre-trained PE diagnosis and detection AI model to new medical images to render a prediction as to the presence or absence of a Pulmonary Embolism within the new medical images comprises:
applying an image-level classification procedure individually to each one of the new medical images to determine, for each one of the new medical images, either the Pulmonary Embolism is present within the respective one of the new medical images or the Pulmonary Embolism is absent from the respective one of the new medical images.

13. The computer-implemented method of claim 8, wherein pre-training an AI model through supervised learning to identify ground truth comprises applying pre-training via self-supervised learning using a publically available dataset having training images annotated as either PE presence or PE absence.

14. The computer-implemented method of claim 8, wherein receiving a plurality of medical images comprises executing instructions for receiving a training dataset having included therein the plurality of medical images; and
wherein the computer-implemented method further enlarges the training dataset's size beyond a received size for the training dataset by:
reshaping each of the plurality of images of the training dataset into a sequence of patches;
upscaling a corresponding image for each patch within the sequence of patches to generate an increased quantity of patches; and
wherein pre-training the AI model through supervised learning to identify ground truth comprises executing instructions for pre-training the AI model through supervised learning using the increased quantity of patches as an enlarged training dataset.

15. Non-transitory computer readable storage media having instructions stored thereupon that, when executed by a processor of a system specially configured for diagnosing a Pulmonary Embolism (PE), the instructions cause the system to perform operations including:
receiving a plurality of medical images;
processing the plurality of medical images by executing an image-level classification algorithm to determine the presence or absence of Pulmonary Embolism (PE) within each image;
pre-training an AI model through supervised learning to identify ground truth;
fine-tuning the pre-trained AI model specifically for PE diagnosis to generate a pre-trained PE diagnosis and detection AI model;
wherein the pre-trained AI model is based on a modified CNN architecture having introduced therein a squeeze and excitation (SE) block enabling the CNN architecture to extract informative features from the plurality of medical images by fusing spatial and channel-wise information;
applying the pre-trained PE diagnosis and detection AI model to new medical images to render a prediction as to the presence or absence of a Pulmonary Embolism within the new medical images; and
outputting the prediction as a PE diagnosis for a medical patient.

16. The non-transitory computer readable storage media of claim 15, wherein the new medical images constitute no part of any training set of medical images utilized to pre-train or fine-tune the AI model and have not been encountered by the pre-trained AI model prior to applying the pre-trained PE diagnosis and detection AI model to the new medical images.

17. The non-transitory computer readable storage media of claim 15, wherein the instructions cause the system to perform operations further comprising:
pre-training a vision transformer (ViT) architecture with a training image dataset; and
upscaling each image in the training image dataset for a given patch size to increase the number of patches resulting in an enlarged size of the training image dataset.

18. The non-transitory computer readable storage media of claim 15, wherein the instructions cause the system to perform operations further comprising:
pre-training an AI model using different sized images generated from the upscaling of each image in the training image dataset for a given patch size; and
wherein applying the pre-trained PE diagnosis and detection AI model to new medical images to render a prediction as to the presence or absence of a Pulmonary Embolism within the new medical images comprises applying an image-level classification procedure individually to each one of the new medical images to determine, for each one of the new medical images, either the Pulmonary Embolism is present within the respective one of the new medical images or the Pulmonary Embolism is absent from the respective one of the new medical images.

19. The non-transitory computer readable storage media of claim 15, wherein pre-training an AI model through supervised learning to identify ground truth comprises applying pre-training via self-supervised learning using a publically available dataset having training images annotated as either PE presence or PE absence.

20. The non-transitory computer readable storage media of claim 15, wherein receiving a plurality of medical images comprises executing instructions for receiving a training dataset having included therein the plurality of medical images; and
wherein the computer-implemented method further enlarges the training dataset's size beyond a received size for the training dataset by:
reshaping each of the plurality of images of the training dataset into a sequence of patches;
upscaling a corresponding image for each patch within the sequence of patches to generate an increased quantity of patches; and
wherein pre-training the AI model through supervised learning to identify ground truth comprises executing instructions for pre-training the AI model through supervised learning using the increased quantity of patches as an enlarged training dataset.

\* \* \* \* \*